(12) United States Patent
Taylor et al.

(10) Patent No.: US 6,939,950 B2
(45) Date of Patent: Sep. 6, 2005

(54) BOVINE TUMOR NECROSIS FACTOR RECEPTOR-1 AND METHODS OF USE

(75) Inventors: Michael J. Taylor, Corvallis, OR (US); Marcus E. Kehrli, Jr., Terre Haute, IN (US); Eun-Kyung Lee, Taegu (KR); Simon Mwangi, Ames, IA (US)

(73) Assignees: Iowa State University Research Foundation, Ames, IA (US); The United States of America as represented by the Department of Agriculture, Washington, DC (US)

( * ) Notice: Subject to any disclaimer, the term of this patent is extended or adjusted under 35 U.S.C. 154(b) by 337 days.

(21) Appl. No.: 09/970,532

(22) Filed: Oct. 3, 2001

(65) Prior Publication Data

US 2002/0076765 A1 Jun. 20, 2002

Related U.S. Application Data

(62) Division of application No. 09/513,007, filed on Feb. 25, 2000, now Pat. No. 6,406,907.
(60) Provisional application No. 60/122,156, filed on Feb. 26, 1999.

(51) Int. Cl.$^7$ .................. C07K 14/715; C07H 21/04
(52) U.S. Cl. .................. 530/350; 536/23.5; 435/69.1
(58) Field of Search .................. 530/350; 536/23.5; 435/69.1; 563/23.5

(56) References Cited

U.S. PATENT DOCUMENTS 5,665,859 A * 9/1997 Wallach et al. ............. 530/328
5,710,124 A   1/1998 Peel et al.

OTHER PUBLICATIONS

Abraham et al., *Lancet*, 1998, 351(9107):929–933.
Björnberg et al., *Lymph. Cyto. Res.*, 1994, 13(3):203–211.
Evans et al., *J. Exp. Med.*, 1994, 180(6):2173–2179.
Gatanaga et al., *Proc. Natl. Acad. Sci. USA*, 1990, 87(22):8781–8784.
Goodwin et al., *Mol. Cell. Biol.*, 1991, 11(6):3020–3026.
Himmler et al., *DNA Cell Biol.*, 1990, 9(10):705–715.
Jones et al., *Biochemistry.*, 1997, 36(48):14914–14923.
Lee et al., *Vet. Immunol. Immunopath.*, 1998, 61:379–385.
Lesslauer et al., *Eur. J. Immunol.*, 1991, 21(11):2883–2886.
Loetscher et al., *Cell*, 1990, 61(2):351–359.
Maroushek–Boury et al., *Am. J. Vet. Res.*, 1998, 59(10):1317–1322.
Mohler et al., *J. Immunol.*, 1993, 151(3):1548–1561.
Schall et al., *Cell*, 1990, 61:361–370.
Shuster et al., *Am. J. Vet. Res.*, 1993, 54(1):80–85.
Shuster et al., *Am. J. Vet. Res.*, 1995, 56(3):313–320.
Shuster et al., *Am. J. Vet. Res.*, 1996, 57(11):1569–1575.
Sileghem et al., *Hybridoma*, 1992, 11(5):617–627.
Smith et al., *Science*, 1990, 248:1019–1023.
Sordillo et al., *J. Dairy Sci.*, 1992, 75(8):2119–2125.
Suter et al., *Gene*, 1995, 163(2):263–266.
Van Zee et al., *Proc. Natl. Acad. Sci. USA*, 1992, 89(11):4845–4849.

* cited by examiner

*Primary Examiner*—Lorraine Spector
*Assistant Examiner*—Eileen B. O'Hara
(74) *Attorney, Agent, or Firm*—Fish & Richardson P.C., P.A.

(57) ABSTRACT

The invention relates to nucleic acid sequences encoding a bovine tumor necrosis factor receptor-I (TNF-RI). Also within the invention is a soluble bovine TNF-RI, which is a potent inhibitor of bovine tumor necrosis factor-α (TNF-α). The invention demonstrates that soluble bovine TNF-RI has therapeutic value as an inhibitor of TNF in cattle suffering from coliform mastitis or other inflammatory disease.

16 Claims, 3 Drawing Sheets

Fig. 1

SEQUENCE LISTING

<160> NUMBER OF SEQ ID NOS: 8

<210> SEQ ID NO 1
<211> LENGTH: 2440
<212> TYPE: DNA
<213> ORGANISM: Bos taurus
<220> FEATURE:
<221> NAME/KEY: CDS
<222> LOCATION: (294)...(1706)

<400> SEQUENCE: 1

-continued

| | |
|---|---|
| tttttattttt tttttttcttt ttttgggggg gaaagggtg accccccttc ccctcccacc | 60 |
| tcctctcagc tcaagttttc tcggagctct ccgggctctg ggccgcaggg ctggccttcc | 120 |
| gggtttgagg tcctccggat tgggctgtgt ccccgcccca gtctcaaccc tccactcccc | 180 |
| gacccgaggc ccgggctcca ctgggcatac gcgaggaccg tgttgctgtc actgtcgcgg | 240 |
| gccgccactg ccccagccct gatgggggat tgagaggcca cagctggccg gac atg | 296 |

```
                                                                  Met
                                                                   1 ggc ctc ccc acc gtg cct ggc ctg ctg ctg cca ctg gtg ctt cca gct      344
Gly Leu Pro Thr Val Pro Gly Leu Leu Leu Pro Leu Val Leu Pro Ala
            5                  10                  15 ctg ttg gca gat gtg tac ccc gca ggg gtt cag ggg ctg gtc cct cac      392
Leu Leu Ala Asp Val Tyr Pro Ala Gly Val Gln Gly Leu Val Pro His
        20                  25                  30 ccc ggg gac ctg gag aag aga gag agt ccc tgt ccc caa gga aaa tat      440
Pro Gly Asp Leu Glu Lys Arg Glu Ser Pro Cys Pro Gln Gly Lys Tyr
    35                  40                  45 aac cac ccg caa aat agc acc att tgc tgc acc aag tgc cac aaa ggt      488
Asn His Pro Gln Asn Ser Thr Ile Cys Cys Thr Lys Cys His Lys Gly
 50                  55                  60                  65 acc tat ctg tac aat gac tgt ccg ggt cca ggg cga gac acg gac tgc      536
Thr Tyr Leu Tyr Asn Asp Cys Pro Gly Pro Gly Arg Asp Thr Asp Cys
                70                  75                  80 agg gtg tgt gcc cct ggc acc tac act gcc ttg gag aac cat ctc aga      584
Arg Val Cys Ala Pro Gly Thr Tyr Thr Ala Leu Glu Asn His Leu Arg
            85                  90                  95 cga tgc ctg agc tgc tcc agg tgc cgg gac gaa atg ttc cag gtg gag      632
Arg Cys Leu Ser Cys Ser Arg Cys Arg Asp Glu Met Phe Gln Val Glu
        100                 105                 110 att tcg cct tgt gta gtg gac cgg gac act gtg tgc ggc tgc agg aag      680
Ile Ser Pro Cys Val Val Asp Arg Asp Thr Val Cys Gly Cys Arg Lys
    115                 120                 125 aac cag tac cgg gaa tac tgg ggt gaa act ggc ttc cgg tgt ctg aac      728
Asn Gln Tyr Arg Glu Tyr Trp Gly Glu Thr Gly Phe Arg Cys Leu Asn
130                 135                 140                 145 tgc agc ctc tgt ccc aat ggc aca gtg aat atc ccc tgc cag gag aga      776
Cys Ser Leu Cys Pro Asn Gly Thr Val Asn Ile Pro Cys Gln Glu Arg
                150                 155                 160 cag gac acc atc tgc cac tgc cat atg ggc ttc ttt ctt aaa ggc gcc      824
Gln Asp Thr Ile Cys His Cys His Met Gly Phe Phe Leu Lys Gly Ala
            165                 170                 175 aag tgc atc tcc tgt cat gat tgt aag aac aag gag tgc gag aag tta      872
Lys Cys Ile Ser Cys His Asp Cys Lys Asn Lys Glu Cys Glu Lys Leu
        180                 185                 190 tgt cca acc cga cct tca act ggt aaa gac tct cag gac cca ggc act      920
Cys Pro Thr Arg Pro Ser Thr Gly Lys Asp Ser Gln Asp Pro Gly Thr
    195                 200                 205 aca gta cta tta ccc ctg gtg att gtc ttc ggg ctt tgc ctg gca tcc      968
Thr Val Leu Leu Pro Leu Val Ile Val Phe Gly Leu Cys Leu Ala Ser
210                 215                 220                 225 ttc gcc tct gtc gtc tta gca tgt cgc tac cag cgg tgg aag ccc aag     1016
Phe Ala Ser Val Val Leu Ala Cys Arg Tyr Gln Arg Trp Lys Pro Lys
                230                 235                 240 ctc tac tcc atc att tgc ggg cag tcg act ctg gta aaa gag ggg gag     1064
Leu Tyr Ser Ile Ile Cys Gly Gln Ser Thr Leu Val Lys Glu Gly Glu
            245                 250                 255 cca gaa ctc ctg gtc ccg gcc cca ggc ttc aac ccc acc acc acc atc     1112
Pro Glu Leu Leu Val Pro Ala Pro Gly Phe Asn Pro Thr Thr Thr Ile
```

-continued

```
              260                 265                 270
tgc ttc agc tcc acc cca agt tcc agt cct gtc tcc att ccc cct tac      1160
Cys Phe Ser Ser Thr Pro Ser Ser Pro Val Ser Ile Pro Pro Tyr
    275                 280                 285 atc tcc tgt gac cgg tcc aac ttc gga gcc gtc gca tct ccc tcc agc      1208
Ile Ser Cys Asp Arg Ser Asn Phe Gly Ala Val Ala Ser Pro Ser Ser
290                 295                 300                 305 gag acg gcc ccg ccc cat cta aag gct ggc ccc atc ctc ccg ggg cct      1256
Glu Thr Ala Pro Pro His Leu Lys Ala Gly Pro Ile Leu Pro Gly Pro
                310                 315                 320 ccg gcc tcc acc cac ctc tgt acc ccg ggg cct ccg gcc tcc acc cac      1304
Pro Ala Ser Thr His Leu Cys Thr Pro Gly Pro Pro Ala Ser Thr His
            325                 330                 335 ctc tgt acc ccg ggg cct ccg gcc tcc acc cac ctc tgc acc cca gtt      1352
Leu Cys Thr Pro Gly Pro Pro Ala Ser Thr His Leu Cys Thr Pro Val
        340                 345                 350 cag aag tgg gaa gcc agc gcc ccc agc gcc ccc gat cag ctc gcg gat      1400
Gln Lys Trp Glu Ala Ser Ala Pro Ser Ala Pro Asp Gln Leu Ala Asp
    355                 360                 365 gcc gac ccc gcg acc ctg tac gcg gtg gtg gac ggc gtg ccc ccg tcg      1448
Ala Asp Pro Ala Thr Leu Tyr Ala Val Val Asp Gly Val Pro Pro Ser
370                 375                 380                 385 cgc tgg aag gag ttg gtg cgg cgg ctg gga ctg agc gag cac gag atc      1496
Arg Trp Lys Glu Leu Val Arg Arg Leu Gly Leu Ser Glu His Glu Ile
                390                 395                 400 gag cgg ctg gag ctg gag aac ggg cgc cac ctg cgc gag gcg cag tac      1544
Glu Arg Leu Glu Leu Glu Asn Gly Arg His Leu Arg Glu Ala Gln Tyr
            405                 410                 415 agc atg ctg gcg gcc tgg cgg cgg cgc acg ccg cgc cgc gag gcc acg      1592
Ser Met Leu Ala Ala Trp Arg Arg Arg Thr Pro Arg Arg Glu Ala Thr
        420                 425                 430 ctg gag ctg ctg ggc cgc gtg ctc agg gac atg gac ctg ctg ggt tgc      1640
Leu Glu Leu Leu Gly Arg Val Leu Arg Asp Met Asp Leu Leu Gly Cys
    435                 440                 445 ctg gaa aac ata gag gag gcg ctg ggt ggc gcc gcc cgc ctc gcg tcc      1688
Leu Glu Asn Ile Glu Glu Ala Leu Gly Gly Ala Ala Arg Leu Ala Ser
450                 455                 460                 465 gag ccc cgc ctt ctc tgg tgaagccccg ccctccgac tgcgggcctc             1736
Glu Pro Arg Leu Leu Trp
                470 cccgccctgc agacggctgc ttccttcctg tgccaggcag cccggaagga tctgcgagat   1796 gccctgtgga cctcctgttt tgttttgttt tttctggag aggaagtctt ggaggagcag    1856 gcacgatctg gcagccactg acctggtgct actcactcag tgtacatagc ttttctcagc   1916 tgcctgagtg tgtgtctgtg tgtagtgtgt gtctgcgtgc agtgcgtgtg tttgtgtctc   1976 tgtatgtgcg tctgtgtgat gtggagtgtg tgtactcgtg agagaggccg agtgtgcccg   2036 gagcccaagg cagtggttgc gaagatgagg ggcgccctgc cttattgcct gttttttggg   2096 cttggagaac tcagcaaggc gacttgggga acctacgtcg gtccctgagc cggtttcgca   2156 gtagataagc catctttgta tccactctgc acatccactc atccactctg tacactaata   2216 gaaactttgt tgccctgcct ggaccagctg aactgtcccc aggcagcggg ggagcacaga   2276 aaaatggggc ctcccaaggg agctagctgt tcagttcagt tcagtcgctc agtcgtgtcc   2336 gactctttgc gaccctgtga atcgcaggga cttctgtaaa tacactaaaa tcttccaatt   2396 aaagctctgc cctggaggga ctggttaaaa aaaaaaaaaa aaaa                    2440
```

<210> SEQ ID NO 2
<211> LENGTH: 471
<212> TYPE: PRT
<213> ORGANISM: Bos taurus

<400> SEQUENCE: 2

```
Met Gly Leu Pro Thr Val Pro Gly Leu Leu Pro Leu Val Leu Pro
 1               5                  10                  15

Ala Leu Leu Ala Asp Val Tyr Pro Ala Gly Val Gln Gly Leu Val Pro
                20                  25                  30

His Pro Gly Asp Leu Glu Lys Arg Glu Ser Pro Cys Pro Gln Gly Lys
            35                  40                  45

Tyr Asn His Pro Gln Asn Ser Thr Ile Cys Cys Thr Lys Cys His Lys
        50                  55                  60

Gly Thr Tyr Leu Tyr Asn Asp Cys Pro Gly Pro Gly Arg Asp Thr Asp
 65                  70                  75                  80

Cys Arg Val Cys Ala Pro Gly Thr Tyr Thr Ala Leu Glu Asn His Leu
                85                  90                  95

Arg Arg Cys Leu Ser Cys Ser Arg Cys Arg Asp Glu Met Phe Gln Val
                100                 105                 110

Glu Ile Ser Pro Cys Val Val Asp Arg Asp Thr Val Cys Gly Cys Arg
            115                 120                 125

Lys Asn Gln Tyr Arg Glu Tyr Trp Gly Glu Thr Gly Phe Arg Cys Leu
130                 135                 140

Asn Cys Ser Leu Cys Pro Asn Gly Thr Val Asn Ile Pro Cys Gln Glu
145                 150                 155                 160

Arg Gln Asp Thr Ile Cys His Cys His Met Gly Phe Phe Leu Lys Gly
                165                 170                 175

Ala Lys Cys Ile Ser Cys His Asp Cys Lys Asn Lys Glu Cys Glu Lys
                180                 185                 190

Leu Cys Pro Thr Arg Pro Ser Thr Gly Lys Asp Ser Gln Asp Pro Gly
            195                 200                 205

Thr Thr Val Leu Leu Pro Leu Val Ile Val Phe Gly Leu Cys Leu Ala
210                 215                 220

Ser Phe Ala Ser Val Val Leu Ala Cys Arg Tyr Gln Arg Trp Lys Pro
225                 230                 235                 240

Lys Leu Tyr Ser Ile Ile Cys Gly Gln Ser Thr Leu Val Lys Glu Gly
                245                 250                 255

Glu Pro Glu Leu Leu Val Pro Ala Pro Gly Phe Asn Pro Thr Thr Thr
            260                 265                 270

Ile Cys Phe Ser Ser Thr Pro Ser Ser Pro Val Ser Ile Pro Pro
            275                 280                 285

Tyr Ile Ser Cys Asp Arg Ser Asn Phe Gly Ala Val Ala Ser Pro Ser
290                 295                 300

Ser Glu Thr Ala Pro Pro His Leu Lys Ala Gly Pro Ile Leu Pro Gly
305                 310                 315                 320

Pro Pro Ala Ser Thr His Leu Cys Thr Pro Gly Pro Ala Ser Thr
                325                 330                 335

His Leu Cys Thr Pro Gly Pro Ala Ser Thr His Leu Cys Thr Pro
            340                 345                 350

Val Gln Lys Trp Glu Ala Ser Ala Pro Ser Ala Pro Asp Gln Leu Ala
            355                 360                 365

Asp Ala Asp Pro Ala Thr Leu Tyr Ala Val Val Asp Gly Val Pro Pro
370                 375                 380
```

```
Ser Arg Trp Lys Glu Leu Val Arg Arg Leu Gly Leu Ser Glu His Glu
385                 390                 395                 400

Ile Glu Arg Leu Glu Leu Glu Asn Gly Arg His Leu Arg Glu Ala Gln
            405                 410                 415

Tyr Ser Met Leu Ala Ala Trp Arg Arg Thr Pro Arg Arg Glu Ala
            420                 425                 430

Thr Leu Glu Leu Leu Gly Arg Val Leu Arg Asp Met Asp Leu Leu Gly
            435                 440                 445

Cys Leu Glu Asn Ile Glu Glu Ala Leu Gly Gly Ala Ala Arg Leu Ala
            450                 455                 460

Ser Glu Pro Arg Leu Leu Trp
465                 470

<210> SEQ ID NO 3
<211> LENGTH: 543
<212> TYPE: DNA
<213> ORGANISM: Bos taurus
<220> FEATURE:
<221> NAME/KEY: CDS
<222> LOCATION: (1)...(543)

<400> SEQUENCE: 3 ctg gtc cct cac ccc ggg gac ctg gag aag aga gag agt ccc tgt ccc      48
Leu Val Pro His Pro Gly Asp Leu Glu Lys Arg Glu Ser Pro Cys Pro
 1               5                  10                  15 caa gga aaa tat aac cac ccg caa aat agc acc att tgc tgc acc aag      96
Gln Gly Lys Tyr Asn His Pro Gln Asn Ser Thr Ile Cys Cys Thr Lys
            20                  25                  30 tgc cac aaa ggt acc tat ctg tac aat gac tgt ccg ggt cca ggg cga     144
Cys His Lys Gly Thr Tyr Leu Tyr Asn Asp Cys Pro Gly Pro Gly Arg
        35                  40                  45 gac acg gac tgc agg gtg tgt gcc cct ggc acc tac act gcc ttg gag     192
Asp Thr Asp Cys Arg Val Cys Ala Pro Gly Thr Tyr Thr Ala Leu Glu
    50                  55                  60 aac cat ctc aga cga tgc ctg agc tgc tcc agg tgc cgg gac gaa atg     240
Asn His Leu Arg Arg Cys Leu Ser Cys Ser Arg Cys Arg Asp Glu Met
65                  70                  75                  80 ttc cag gtg gag att tcg cct tgt gta gtg gac cgg gac act gtg tgc     288
Phe Gln Val Glu Ile Ser Pro Cys Val Val Asp Arg Asp Thr Val Cys
                85                  90                  95 ggc tgc agg aag aac cag tac cgg gaa tac tgg ggt gaa act ggc ttc     336
Gly Cys Arg Lys Asn Gln Tyr Arg Glu Tyr Trp Gly Glu Thr Gly Phe
            100                 105                 110 cgg tgt ctg aac tgc agc ctc tgt ccc aat ggc aca gtg aat atc ccc     384
Arg Cys Leu Asn Cys Ser Leu Cys Pro Asn Gly Thr Val Asn Ile Pro
        115                 120                 125 tgc cag gag aga cag gac acc atc tgc cac tgc cat atg ggc ttc ttt     432
Cys Gln Glu Arg Gln Asp Thr Ile Cys His Cys His Met Gly Phe Phe
    130                 135                 140 ctt aaa ggc gcc aag tgc atc tcc tgt cat gat tgt aag aac aag gag     480
Leu Lys Gly Ala Lys Cys Ile Ser Cys His Asp Cys Lys Asn Lys Glu
145                 150                 155                 160 tgc gag aag tta tgt cca acc cga cct tca act ggt aaa gac tct cag     528
Cys Glu Lys Leu Cys Pro Thr Arg Pro Ser Thr Gly Lys Asp Ser Gln
                165                 170                 175 gac cca ggc act aca                                                 543
Asp Pro Gly Thr Thr
            180

<210> SEQ ID NO 4
```

```
<211> LENGTH: 181
<212> TYPE: PRT
<213> ORGANISM: Bos taurus

<400> SEQUENCE: 4

Leu Val Pro His Pro Gly Asp Leu Glu Lys Arg Glu Ser Pro Cys Pro
  1               5                  10                  15

Gln Gly Lys Tyr Asn His Pro Gln Asn Ser Thr Ile Cys Cys Thr Lys
             20                  25                  30

Cys His Lys Gly Thr Tyr Leu Tyr Asn Asp Cys Pro Gly Pro Gly Arg
         35                  40                  45

Asp Thr Asp Cys Arg Val Cys Ala Pro Gly Thr Tyr Thr Ala Leu Glu
 50                  55                  60

Asn His Leu Arg Arg Cys Leu Ser Cys Ser Arg Cys Arg Asp Glu Met
 65                  70                  75                  80

Phe Gln Val Glu Ile Ser Pro Cys Val Val Asp Arg Asp Thr Val Cys
                 85                  90                  95

Gly Cys Arg Lys Asn Gln Tyr Arg Glu Tyr Trp Gly Glu Thr Gly Phe
            100                 105                 110

Arg Cys Leu Asn Cys Ser Leu Cys Pro Asn Gly Thr Val Asn Ile Pro
            115                 120                 125

Cys Gln Glu Arg Gln Asp Thr Ile Cys His Cys His Met Gly Phe Phe
130                 135                 140

Leu Lys Gly Ala Lys Cys Ile Ser Cys His Asp Cys Lys Asn Lys Glu
145                 150                 155                 160

Cys Glu Lys Leu Cys Pro Thr Arg Pro Ser Thr Gly Lys Asp Ser Gln
                165                 170                 175

Asp Pro Gly Thr Thr
            180

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide for PCR

<400> SEQUENCE: 5
agtgtgtgtc cccaaggaaa                                              20

<210> SEQ ID NO 6
<211> LENGTH: 19
<212> TYPE: DNA
<213> ORGANISM: Artificial Sequence
<220> FEATURE:
<223> OTHER INFORMATION: Oligonucleotide for PCR

<400> SEQUENCE: 6
gcagccacac acggtgtcc                                               19

<210> SEQ ID NO 7
<211> LENGTH: 45
<212> TYPE: DNA
<213> ORGANISM: Artificial Sequence
<220> FEATURE:
<223> OTHER INFORMATION: Oligonucleotide for PCR

<400> SEQUENCE: 7
tctctcgaga aaagagaggc tgaagctctg gtccctcacc ccggg                  45
```

-continued

```
<210> SEQ ID NO 8
<211> LENGTH: 39
<212> TYPE: DNA
<213> ORGANISM: Artificial sequence
<220> FEATURE:
<223> OTHER INFORMATION: Oligonucleotide for PCR

<400> SEQUENCE: 8
gctctagagc ttatgtagtg cctgggtcct gagagtctt                                39
```

BOVINE TUMOR NECROSIS FACTOR RECEPTOR-1 AND METHODS OF USE

This application claims the benefit of provisional application No. 60/122,156, filed Feb. 26, 1999.

CROSS-REFERENCE TO RELATED APPLICATIONS

This application is a divisional of and claims priority under 35 U.S.C. §120 to U.S. application Ser. No. 09/513,007, filed Feb. 25, 2000 issued as U.S. Pat. No. 6,406,907.

TECHNICAL FIELD

This invention relates to cytokines and cell signaling, and more particularly, to bovine tumor necrosis factor (TNF) receptor-I.

BACKGROUND

Tumor necrosis factor-α (TNF-α) is a pleiotropic cytokine, and is produced by activated macrophages/monocytes and lymphocytes. TNF-α is a potent mediator in inflammatory and immune responses, including the recruitment of leukocytes to injured tissues during bacterial and other microbial infections, and following stimulation with inflammatory substances. When present in excessive quantities, however, TNF-α is known to cause tissue injury, and has been implicated in the pathology associated with several inflammatory and autoimmune diseases.

The biological effects of TNF are mediated through two distinct receptors, TNF-RI and TNF-RII (in humans, p55 and p75, respectively), which differ in sequence and molecular mass. TNF-RI is reported to he present at low levels in most, if not all, human cell types, and expression of the gene in humans can be upregulated by infection, interferons, and modulators of second messengers, such as phorbol esters. The extracellular portions of both receptors also exist in soluble forms, which are derived by proteolytic cleavage from the cell surface. The soluble TNF receptors retain the ability to bind TNF in solution. Activated cells often shed their TNF receptors, which can render the target cell less sensitive to the biological effects of TNF. Soluble TNF receptors have been identified in urine and sera from healthy individuals, and have been shown to be elevated in some chronic diseases and following inoculation with agents that induce TNF-α release.

SUMMARY

The present invention describes the cloning and characterization of nucleic acid encoding the bovine tumor necrosis factor receptor-I (TNF-RI). Additionally, a soluble bovine TNF-RI was produced and demonstrated to be a potent inhibitor of bovine tumor necrosis factor α (TNF-α). The availability of nucleic acid sequences encoding the bovine TNF-RI, particularly those nucleic acid sequences encoding a soluble form, provides a therapeutic compound for preventing and treating inflammatory diseases in bovine animals.

In general, the invention features an isolated nucleic acid, such as (a) the nucleotide sequence of SEQ ID NO:1; (b) a fragment of the nucleotide sequence of (a) encoding a functional polypeptide fragment; (c) a nucleotide sequence that is at least 85% identical to (a) or (b); or (d) a nucleotide sequence complementary to (a), (b) or (c). For instance, the nucleotide sequence may be at least 90% identical, or at least 95% identical, to (a) or (b). The nucleic acid may encode a bovine tumor necrosis factor receptor-I (TNF-RI), which may bind tumor necrosis factor (TNF). The nucleic acid may encode, for example, a TNF-RI having the amino acid sequence of SEQ ID NO:2.

The invention also features a nucleic acid such as (a) the nucleotide sequence shown in SEQ ID NO:3; (b) a fragment of the nucleotide sequence of (a) encoding a functional polypeptide fragment; (c) a nucleotide sequence that is at least 85% identical to (a) or (b); or (d) a nucleotide sequence complementary to (a), (b) or (c). The nucleic acid may encode a soluble bovine TNF-RI, which may bind TNF. The nucleic acid may encode, for example, a soluble bovine TNF-RI having the amino acid sequence of SEQ ID NO:4.

Additionally, there are provided vectors that include one or more of the above-described nucleic acids. The vector(s) may include elements necessary for expression of the above-described nucleic acids operably linked to the nucleic acid (s). The invention further provides host cells containing such vectors.

The invention also features isolated bovine TNF-RI and soluble bovine TNF-RI polypeptides. Additionally, antibodies that have specific binding affinity for the bovine TNF-RI and soluble bovine TNF-RI polypeptides are provided. A feature of the invention is a soluble bovine TNF-RI, which may include a bovine TNF-RI extracellular domain or fragments thereof. The soluble bovine TNF-RI may further bind TNF.

Yet another feature of the invention is an isolated nucleic acid encoding a fusion protein. Within the context of the present invention, the fusion protein may be encoded by a nucleic acid encoding a soluble bovine TNF-RI and a second nucleic acid sequence. For example, the second nucleic acid sequence may be an antibody or fragment thereof.

The invention also features a method of inhibiting TNF cytotoxicity in a bovine animal, and includes administering an effective amount of a polypeptide or a nucleic acid encoding the polypeptide to the animal. In the context of the present invention, the polypeptide is one or more soluble, functional polypeptide fragments of bovine TNF-RI that bind TNF and thereby inhibit TNF cytotoxicity in the bovine animal. For example, soluble, functional polypeptide fragments of bovine TNF-RI may be administered by direct infusion, and further, may be directly infused into the animal's mammary gland. In the context of the present invention, inhibition of TNF cytotoxicity in the animal is useful, for example, to treat mastitis. The effective amount may be, for example, from about 1 µg/kg body weight to about 1 mg/kg body weight.

Another feature of the invention is a pharmaceutical composition, including one or more soluble, functional polypeptide fragments of bovine TNF-RI and a pharmaceutically acceptable carrier. Also provided is a kit, which includes at least one unit dose of the above-described pharmaceutical composition.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable, but not necessarily preferred, methods and materials are described below. In addition, the materials, methods and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DESCRIPTION OF DRAWINGS

FIG. 1 is the nucleotide sequence and the deduced amino acid sequence of a bovine tumor necrosis factor receptor-I (TNF-RI) cDNA (SEQ ID NO:1; GenBank Accession No. U90937). A solid line indicates the hydrophobic signal peptide and a dashed line indicates the transmembrane region. Within the extracellular domain, the cysteine residues are circled and N-linked glycosylation sites are boxed.

Like reference symbols in the various drawings indicate like elements.

DETAILED DESCRIPTION

Figure 2:
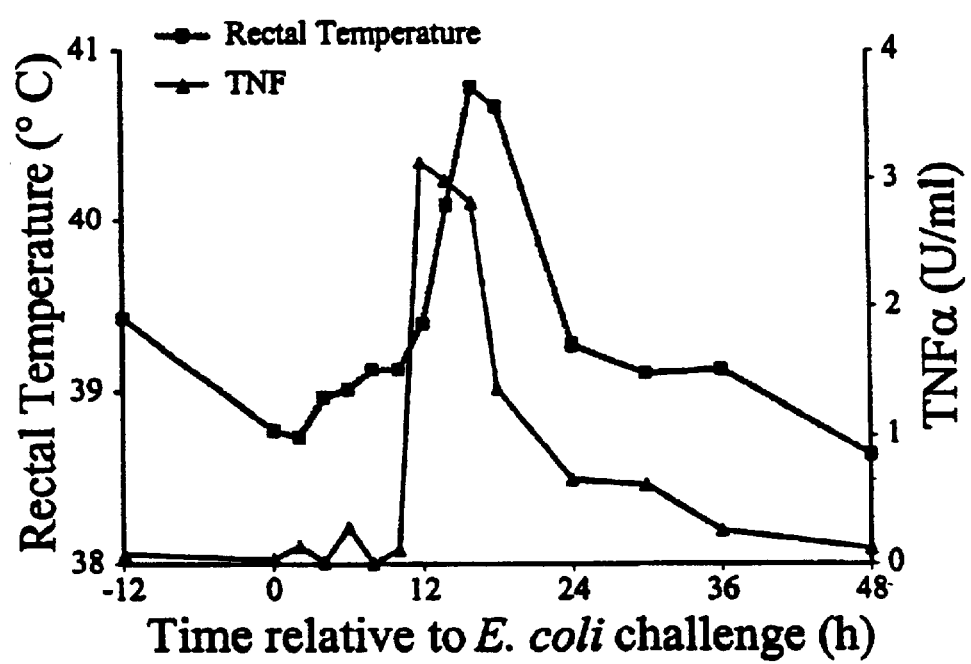
FIG. 2 is a graph showing the presence of tumor necrosis factor (TNF) in bovine mammary gland prior to and following the onset of a febrile response to *Escherichia coli* challenge of one quarter of the mammary gland.

The invention relates to a bovine tumor necrosis factor receptor-I (TNF-RI), and more specifically, a soluble bovine TNF-RI, which is a potent inhibitor of bovine TNF-α. This invention demonstrates that soluble bovine TNF-RI has therapeutic value as an inhibitor of tumor necrosis factor (TNF) in cattle suffering from coliform mastitis or other inflammatory disease.

Bovine TNF receptor-I

In one aspect, the invention features an isolated nucleic acid encoding a bovine tumor necrosis factor receptor-I (TNF-RI), or the complement thereof As used herein, "isolated" refers to a nucleotide sequence encoding part or all of the bovine TNF-RI, but free of sequences that normally flank one or both sides of nucleic acid sequences encoding bovine TNF-RI in the bovine genome. The term "TNF-RI" refers to a receptor in which the extracellular domain binds TNF and propagates a signal to the cell via the intracellular domain. Typically, TNF-RI is found on most, if not all, bovine cell types, including neutrophils and mononuclear leukocytes.

Figure 1:
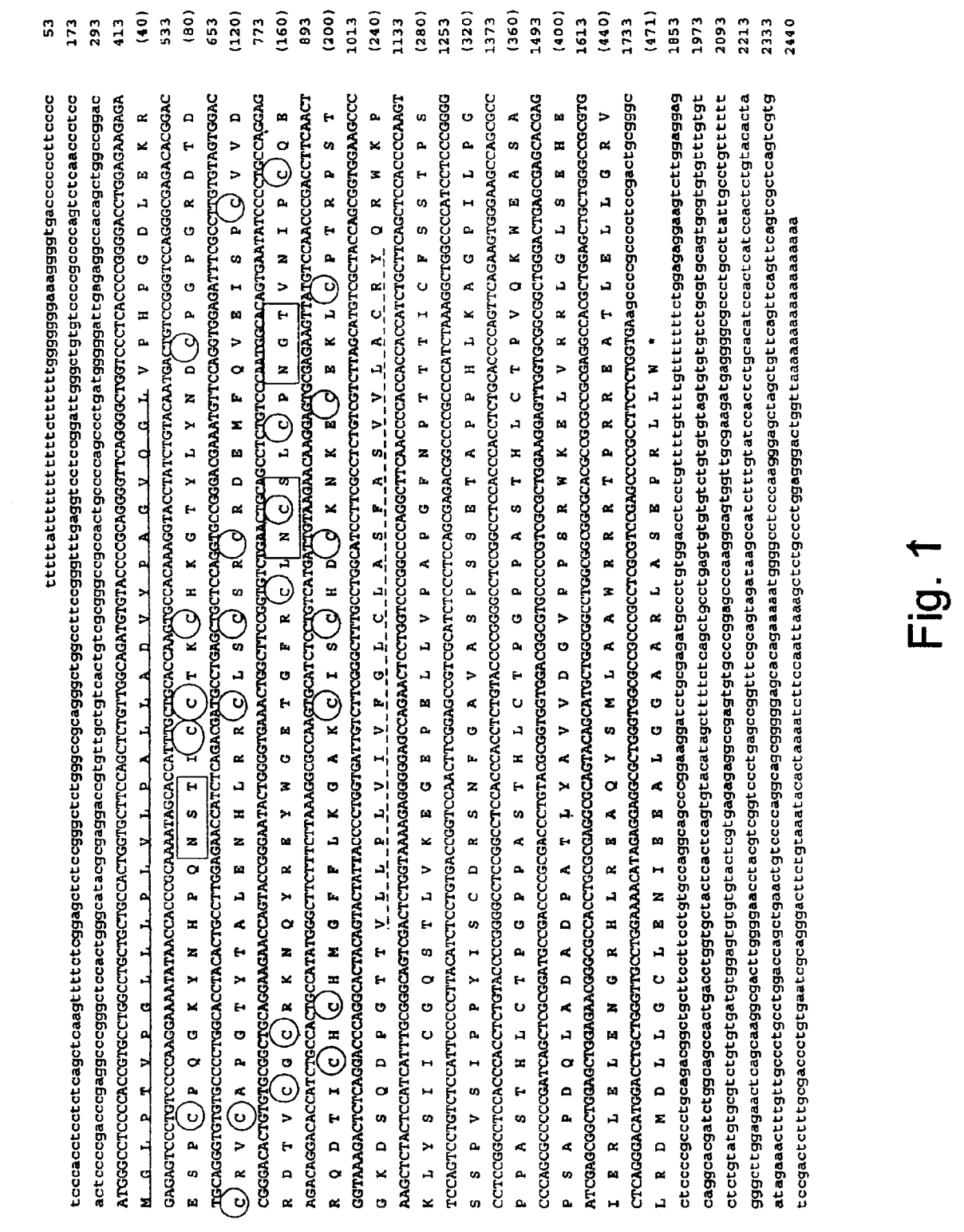

An example of a nucleotide sequence encoding a bovine TNF-RI is shown in FIG. 1 (SEQ ID NO:1), which is a 2440 bp cDNA having an open reading frame of 1413 nucleotides. The amino acid sequence of a bovine TNF-RI is shown in SEQ ID NO:2, and is 471 amino acids in length. The start codon for the bovine TNF-RI is a methionine corresponding to nucleotide 294 of SEQ ID NO:1 and the protein terminates with a stop codon corresponding to nucleotide 1709. The bovine TNF-RI includes a signal peptide, an extracellular domain, a transmembrane domain and an intracellular domain (FIG. 1).

In another aspect, the invention features a soluble fragment of the bovine TNF-RI, hereinafter referred to as "soluble TNF-RI" or "soluble bovine TNF-RI". As used herein, "soluble" TNF-RI refers to a TNF-RI polypeptide that is water-soluble or soluble in an aqueous solution, preferably having a physiological pH. An example of a nucleotide sequence encoding a soluble bovine TNF-RI is shown in SEQ ID NO:3 and is 543 nucleotides in length. An example of an amino acid sequence of a soluble bovine TNF-RI is shown in SEQ ID NO:4 and consists of 181 amino acids. SEQ ID NO:4 corresponds to the extracellular domain of the full-length bovine TNF-RI (FIG. 1). Typically, a soluble bovine TNF-RI includes the extracellular domain, but may include more or less amino acids, provided that the polypeptide remains soluble.

A bovine TNF-RI or soluble bovine TNF-RI nucleic acid may have a sequence that deviates from that shown in SEQ ID NO:1 or SEQ ID NO:3, respectively. For example, a nucleic acid sequence can have at least 85% sequence identity to the nucleotide sequence of SEQ ID NO:1 or SEQ ID NO:3. In some embodiments, the nucleic acid sequence can have at least 90% sequence identity or at least 95% sequence identity to SEQ ID NO:1 or SEQ ID NO:3.

Generally, percent sequence identity is calculated by determining the number of matched positions in aligned nucleic acid sequences, dividing the number of matched positions by the total number of aligned nucleotides, and multiplying by 100. A matched position refers to a position in which identical nucleotides occur at the same position in aligned nucleic acid sequences. Nucleic acid sequences can be aligned by visual inspection, or by using sequence alignment software, such as the Sequence Analysis Software Package of the Genetics Computer Group, University of Wisconsin Biotechnology Center, 1710 University Avenue, Madison, Wis. 53705, or BLAST programs (provided as a service by the National Center for Biotechnology Information, on the world wide web at ncbi.nlm.nih.gov). The programs are described in detail by Karlin et al., *Proc Natl Acad Sci USA* 87:2264 (1990) and 90:5873 (1993), and Altschul et al., *Nucl Acids Res* 25:3389 (1997). Typically, default parameters and algorithms are used when performing sequence analysis. Sequence analysis of TNF-RI as described herein was performed using BestFit (with a Gap Weight of 5.0 and 3.0 and a Length Weight of 0.3 and 0.1 for nucleic acids and amino acids, respectively).

In another aspect, the invention includes fragments of the bovine TNF-RI nucleic acid and polypeptide. FIG. 1 shows various domains (i.e., intracellular, transmembrane and extracellular) of the bovine TNF-RI nucleic acid and polypeptide that, by way of example, provide useful regions from which to generate fragments. For example, a fragment of a bovine TNF-RI nucleic acid sequence can include from about nucleotide 294 to about nucleotide 1709 of SEQ ID NO:1, from about nucleotide 378 to about nucleotide 923, from about nucleotide 924 to about nucleotide 1001 or from about nucleotide 1002 to about nucleotide 1709. Given the nucleotide sequence of a bovine TNF-RI, virtually any nucleic acid fragment can be generated by known means (e.g., restriction enzyme digestion, the polymerase chain reaction) and, if so desired, expressed to produce the corresponding polypeptide fragment. Alternatively, the bovine TNF-RI polypeptide can be cleaved (e.g., proteolytically) to generate polypeptide fragments directly.

Additionally, "functional polypeptide fragments" of the bovine TNF-RI can be produced. "Functional polypeptide fragments" are defined as polypeptide fragments of bovine TNF-RI that retain the ability to bind bovine TNF. For instance, a polypeptide from about nucleotide 378 to about nucleotide 923 corresponding to the extracellular domain was demonstrated herein to retain the ability to bind TNF. Therefore, the polypeptide encoded by nucleotides 378–923 of SEQ ID NO:1 is an example of a functional polypeptide fragment. The ability of polypeptide fragments to bind TNF may be assayed using the methods described herein.

A nucleic acid encoding a bovine TNF-RI may be obtained from, for example, a cDNA library made from bovine endothelial cells treated with TNF, or can be obtained by other means, including, but not limited to, the polymerase chain reaction (PCR). PCR refers to a procedure or technique in which target nucleic acids are amplified. PCR can be used to amplify specific sequences from DNA as well as RNA, including sequences from total genomic DNA or total cellular RNA. Various PCR methods are described, for example, in *PCR Primer: A Laboratory Manual*, Dieffenbach, C. & Dveksler, G., Eds., Cold Spring Harbor Laboratory Press, 1995. Generally, sequence information from the ends of the region of interest or beyond is employed to design oligonucleotide primers that are identical or similar in sequence to opposite strands of the template to be amplified. Representative oligonucleotide primers are shown in SEQ ID NOS:5, 6, 7 and 8.

Furthermore, bovine TNF-RI nucleic acids can be detected by, for example, a variety of hybridization techniques. Hybridization typically involves Southern or Northern blotting (see, for example, sections 9.37–9.52 of Sambrook et al., 1989, *"Molecular Cloning, A Laboratory Manual"*, $2^{nd}$ Edition, Cold Spring Harbor Press, Plainview; N.Y.). Oligonucleotide fragments can hybridize under moderate stringency conditions, or preferably, under high stringency conditions to a bovine TNF-RI nucleic acid (e.g., DNA or RNA), or the complement thereof. High stringency conditions can include the use of low ionic strength and high temperature washes, for example 0.015 M NaCl/0.0015 M sodium citrate (0.1×SSC), 0.1% sodium dodecyl sulfate (SDS) at 65° C. Alternatively, denaturing agents such as formamide can be employed during hybridization (e.g., 50% formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.).

Bovine TNF Receptor-I Nucleic Acid Constructs

The present invention includes vectors containing the bovine TNF-RI nucleic acid of SEQ ID NO:1 (or the complement thereof), nucleic acids encoding functional polypeptide fragments of SEQ ID NO:1 (e.g., SEQ ID NO:3) (or the complements thereof) and nucleic acids having at least 85% sequence identity to SEQ ID NO:1 (or the complements thereof). Cloning vectors and expression vectors suitable for use in the present invention are commercially available and used routinely by those of skill in the art. Vectors of the invention may additionally comprise elements necessary for expression operably linked to a bovine TNF-RI nucleic acid sequence. Elements necessary for expression include promoter sequences, and additionally may include regulatory elements, such as enhancer sequences, response elements or inducible elements that modulate expression of the bovine TNF-RI nucleic acid sequence. As used herein, "operably linked" refers to positioning of a promoter and/or other regulatory element(s) in a construct relative to the bovine TNF-RI nucleic acid sequences in such a way as to direct or regulate expression of the TNF-RI nucleic acid. Such constructs can be produced by recombinant DNA technology methods routine in the art.

In still another aspect, the invention features nucleic acid sequences encoding a fusion protein containing a soluble bovine TNF-RI and a second polypeptide. The second polypeptide may be an antibody or fragment thereof As used herein, "antibody" refers to whole antibodies of any class, i.e., IgG, IgA, IgM or any other known class and includes portions or fragments of whole antibodies (e.g., Fab fragments) having the desired affinity.

The choice of expression systems depends upon several factors, including, but not limited to, replication efficiency, selectability, inducibility, targeting, the level of expression desired, ease of recovery and the ability of the host to perform post-translational modifications. For instance, the high cysteine content found in the TNF-RI proteins has previously created solubility problems due to improper protein folding when the receptors are expressed in prokaryotic expression hosts (Jones et al., 1997, *Biochemistry* 36:14914–14923, and references therein). The *Pichia pastoris* heterologous gene expression system, on the other hand, has been used successfully to produce large quantities of TNF-RI in a soluble form that have previously been insoluble when expressed in *E. coli*. Using a *Pichia pastoris* expression system, soluble bovine TNF-RI was expressed as a diffuse polypeptide ranging in molecular weight from ~20–25 kDa, each band probably representing a different level of glycosylation of the polypeptide. However, despite producing variously glycosylated polypeptide species, *P. pastoris* has been reported to not hyperglycosylate secreted proteins, which is especially important for proteins that are intended for in vivo use (Tschopp et al., 1987, *BioTechnology* 5:1305–1308).

As used herein, the term "host" or "host cell" is meant to include not only prokaryotes, such as *E. coli*, but also eukaryotes, such as yeast, plant and animal cells. A host cell can be transformed or transfected with a DNA molecule (e.g., a vector) using any of the techniques commonly known to those of ordinary skill in the art. Host cells containing a vector of the present invention may be used for such purposes as propagating the vector, producing bovine TNF-RI nucleic acid (e.g., DNA, RNA, antisense RNA) or expressing the bovine TNF-RI, soluble forms thereof and other functional polypeptide fragments.

Nucleic acids of the present invention may be detected by methods such as Southern blot or Northern blot analysis (i.e., hybridization), polymerase chain reaction (PCR) or in situ hybridization analysis. TNF-RI proteins are typically detected by Western blot analysis (using antibodies (monoclonal or polyclonal) that have specific binding affinity for a bovine TNF-RI polypeptide) or sodium dodecyl sulphate (SDS)-polyacrylamide gel electrophoresis followed by Coomassie Blue-staining.

Therapeutic and Diagnostic Uses for Bovine TNF Receptor-I

The invention also features novel therapeutic and diagnostic uses for the bovine TNF-RI nucleic acids and polypeptides of the present invention. For example, soluble, functional polypeptide fragments of TNF-RI (e.g., soluble bovine TNF-RI, e.g., the extracellular domain of TNF-RI) can be used to therapeutically treat bovine mastitis.

Mastitis is defined as inflammation of the mammary gland. Infectious mastitis is caused by a plethora of microbial agents (Watts, 1988, *Vet Micro* 16:41–66). Veterinarians are routinely called upon to treat cows for mastitis, and nearly half of the nation's herd of 9.5 million dairy cows in the US (USDA estimates for January, 1997) will experience at least one episode of mastitis during each lactation. As used herein, "lactation" refers to the period in which the mammary gland produces milk. Bovine lactation typically lasts approximately 305 to 365 days, followed by 45–60 days of a dry, non-lactating period (to allow, for example, mammary gland "regeneration of tissue" and colostrum formation). At the end of a dry period, a cow calves and begins the lactation cycle again.

Bovine coliform mastitis, characterized by inflammation of the mammary gland due to intramammary infections with gram negative bacteria, is common in dairy cattle during the periparturient and early lactation periods, and is a major cause of lost milk production and reduced milk quality for the dairy industry. Antibiotics play a limited role in treatment of mastitis (e.g., dry cow intramammary therapy or during lactation caused by gram positive bacteria, e.g., *Streptococcus* spp.), and control procedures mainly entail preventing exposure of teat canals to new infections. Antibiotics are ineffective against coliform (i.e., gram negative) bacterial infections, and therefore, there are no approved efficacious treatments for coliform mastitis.

Mastitis-induced hypogalactia is a major financial concern of dairy farmers. Hypogalactia is apparently mediated in part by local factors in the infected quarter of the mammary gland but also by systemic reactions that affect the non-infected quarters of the same mammary gland. Additionally, the problem of coliform mastitis is compounded by the fact that a significant number of intramammary infections with coliform bacteria result in a peracute disease, which is accompanied by severe systemic disturbances and often death.

When mastitis is induced by mammary gland challenge with *E. coli* or endotoxin, TNF is produced and detected in whey before or coincident with physiological (e.g., pyrexia), cellular (e.g., leukocytic influx), and mammary gland (e.g., hypogalactia) responses. FIG. 2 illustrates a temporal relationship between TNF and rectal temperature approximately 12 h after challenge with *E. coli*. Milk TNF-α levels and other inflammatory cytokines have been shown to be greatly elevated during natural or experimental bovine coliform mastitis, while extremely high serum TNF-α concentrations have been associated with acute and peracute coliform mastitis. Production of TNF appears consistently throughout the disease progression and the levels of TNF found in lacteal secretions typically correlate with the clinical severity of disease.

The cloning and sequencing of bovine TNF-RI nucleic acids, as disclosed herein, provides a necessary tool for the expression of soluble forms of bovine TNF-RI to block TNF cytotoxicity locally in the bovine mammary gland. Soluble forms of the bovine TNF-RI polypeptide are also useful for the therapeutic treatment of other bovine inflammatory diseases. The efficacy of the soluble bovine TNF-RI as an inhibitor of TNF-α cytotoxicity is demonstrated herein. Additionally, evidence demonstrating that the soluble bovine TNF-RI is a better inhibitor of bovine TNF-α than monoclonal antibody (MAb) BC9 (an antibody directed towards TNF-α) is significant, since anti-TNF-α monoclonal antibodies have been shown to elicit an anti-globulin response when used in vivo to neutralize TNF-α in humans (Abraham et al., 1998, *Lancet* 351:929–933). Moreover, soluble bovine TNF-RI that binds both TNF-α and TNF-β (lymphotoxin) is more valuable as an anti-TNF agent than antibodies that recognize only one or the other.

In one aspect of the present invention, there is provided a method of inhibiting TNF cytotoxicity in a bovine animal by administering an effective amount of one or more soluble, functional polypeptide fragments of bovine TNF-RI (or one or more nucleic acids encoding soluble, functional polypeptide fragments of bovine TNF-RI) to the animal. The soluble, functional polypeptide fragments of bovine TNF-RI bind TNF and thereby inhibit TNF cytotoxicity. As used herein, "cytotoxicity" refers to cellular toxicity, which is typically measured by cell staining (e.g., healthy cells may exclude a certain dye, whereas dying or dead cells absorb the dye). The routes of administration can depend on a variety of factors, such as the type and location of the infection. It is anticipated that the preferred therapeutic use for soluble, functional polypeptide fragments of bovine TNF-RI are administration of the soluble, functional polypeptide fragment(s) directly into the mammary gland to treat mastitis in the affected quarter(s). Typically, infusion into the mammary gland is via the teat canal. This method of administration (via an infusion tube) is currently performed by dairy farm employees to introduce antibiotics directly into the mammary gland. More general routes of administration, such as intravenous, intramuscular, intraperitoneal, intrauterine, intravaginal, intranasal, intradermal, subcutaneous, topical, or the like are also provided.

A preparation containing at least one soluble, functional polypeptide fragment of bovine TNF-RI can be in any form, provided the preparation can be administered to a bovine animal in an amount and for a duration that is effective to prevent, reduce, and/or eliminate bovine mastitis or other inflammatory disease. For example, preparations of soluble, functional polypeptide fragments of bovine TNF-RI for administration can include solutions, suspensions, emulsions, gels, ointments, creams, powders, pills, capsules and tablets. In addition, preparations within the scope of the invention can contain additional ingredients, including, without limitation, pharmaceutically acceptable aqueous, non-aqueous, and solid vehicles or carriers, therapeutic compounds, steroids, mucolytic agents, other anti-inflammatory agents, immunosuppressants, vasodilators, vasoconstrictors, and/or combinations thereof.

The dosages of soluble, functional polypeptide fragments of bovine TNF-RI depends upon many factors, including the mode of administration and the degree of treatment required (e.g., whether the infection is confined to the mammary gland or has become systemic). Typically, the concentration of soluble, functional polypeptide fragments of bovine TNF-RI contained within a single dose will be an amount that effectively reduces TNF levels without inducing significant toxicity. Generally, a preparation may be infused into the mammary gland in a volume of from about 5 ml to about 30 ml, and may include, by way of example, a dose of from about 10 mg to about 100 mg of soluble, functional polypeptide fragments of bovine TNF-RI. Administered doses of soluble, functional polypeptide fragments of bovine TNF-RI may be lower if, for instance, the soluble, functional polypeptide fragments of bovine TNF-RI are expressed as a fusion protein that ultimately results in an increased binding affinity by the soluble, functional polypeptide fragments for TNF. Infusion regimens for the soluble, functional polypeptide fragments of bovine TNF-RI may include, but are not limited to, the first 2–3 milkings after mastitis is initially recognized in an animal.

The invention will be further described in the following examples, which do not limit the scope of the invention described in the claims.

EXAMPLE 1

Cloning the Nucleic Acid Sequences Encoding the Bovine Tumor Necrosis Factor Receptor-I (TNF-RI)

The following primers were designed for polymerase chain reaction (PCR) amplification from conserved regions among the porcine TNF-RI cDNA: forward primer: 5'-AGTGTGTGTCCCCAAGGAAA-3' (SEQ ID NO:5) and reverse primer: 5'-GCAGCCACACACGGTGTCC-3' (SEQ ID NO:6). A Uni-ZAP™ XR cDNA library (Stratagene, La Jolla, Calif.) of bovine endothelial cells treated with recombinant human TNF-α (rhuTNF-α) was titered, diluted, and used as template for PCR. A 250 bp PCR fragment was amplified from $1.4 \times 10^3$ plaque-forming units (pfu). The DNA fragment was sequenced and showed high homology with porcine and human TNF-RI sequences. This fragment was labeled with $^{32}$P-dCTP using the random priming method (Pharmacia, Piscataway, N.J.) and then used as a probe to screen the bovine endothelial cell cDNA library.

Plaque lifts and phagemid in vivo excision were carried out according to manufacturer's protocols. In short, 1.4×10$^4$ pfus were plated. Plaque hybridization was performed overnight at 42° C. in a solution containing 50% formamide, 6×SSC, 3.3× Denhardt's solution, 0.1 mg/ml sonicated salmon sperm DNA, and 0.4% SDS. Filters were washed twice in 2×SSC/0.1% SDS for 5 min at room temperature (RT), once in 1×SSC/0.1% SDS for 5 min at RT, once in 0.1×SSC/0.1% SDS for 5 min at RT, and a final wash in 0.1×SSC/0.1% SDS for 5 min at 53° C., then exposed at −70° C. for 18 h to X-ray film for autoradiography. Positive plaques were amplified and re-screened. After the second screening, the double-positive λ clones were subjected to in vivo excision. The pBluescript phagemids excised from the λ clones were purified and insert sizes were evaluated by restriction enzyme digestion analysis. One of three positive clones, containing a cDNA insert that was approximately 2.5 Kb, was selected for further characterization.

EXAMPLE 2

Characterization of Bovine TNF-RI

Double-stranded DNA sequencing was performed by automated dideoxy sequencing at the Iowa State University DNA Sequencing Facility. DNA and deduced amino acid sequences were analyzed using the programs in the GCG software package (University of Wisconsin Genetics Computer Group, Inc., Madison, Wis., USA).

The composite cDNA sequence for the bovine TNF-RI coding region (FIG. 1) shows 82% homology with porcine TNF-RI and 77% homology with human TNF-RI. The deduced amino acid sequence for bovine TNF-RI shows 75% and 67% identity with porcine and human TNF-RI, respectively. The bovine TNF-RI amino acid sequence (FIG. 1) consists of a hydrophobic signal peptide (29 amino acids), a cysteine-rich extracellular domain (181 amino acids), a hydrophobic transmembrane region (23 amino acids), and a cytoplasmic tail (238 amino acids). The extracellular domain contains three potential N-glycosylation sites at the same positions as the porcine and human TNF-RI. Furthermore, the extracellular region contains 24 cysteine residues (4 repeated cysteine-rich domains), which are 100% conserved in all species and are consistent with belonging to the TNF receptor family.

Expression of TNF-RI in selected bovine cells and tissues was evaluated by Northern blot analysis. Mononuclear cells (MNC) and neutrophils were separated (Kehrli et al., 1990, Am. J. Vet. Res. 51:1826–1836; Harp et al., 1991, Vet. Immunol. Immunopathol. 28:29–35) and stimulated with pokeweed mitogen for 18 h (PWM; 10 µg/ml) and platelet activating factor for 3 h (PAF; 1 µg/ml), respectively. Lymph node and spleen were homogenized and RNA was extracted without stimulating the cells. Total RNA from cells and tissues was extracted using Trizol (Gibco BRL, Gaithersburg, Md.) and chloroform, precipitated with isopropanol, and washed with 75% ethanol. Twenty µg of total RNA from each sample were electrophoresed through a 1% agarose gel containing formaldehyde, blotted onto nylon membranes, and probed with a $^{32}$P-dCTP random labeled cDNA probe derived from bovine TNF-RI (~1.3 kb of the coding region). Prehybridization, hybridization, and washing conditions were the same as those used for the cDNA library screening.

Detectable expression of TNF-RI mRNA was found in bovine spleen and lymph node tissue, as well as blood mononuclear cells and neutrophils. The size of the transcript detected (~2.4 kb) is consistent with the predicted size of the mRNA derived from the cloned cDNA. These data confirm that the TNF-RI gene is present and expressed in bovine cells of immune lineage.

EXAMPLE 3

Expression and Purification of Soluble Bovine TNF-RI

The sequence encoding the putative extracellular domain of bovine TNF-RI was amplified by PCR from the cloned bovine TNF-RI cDNA (Lee et al., 1998, Vet. Immunol. Immunopathol. 61:379–385) using an upstream primer (5'-TCTCTCGAGAAAAGAGAGGCTGAAGCTCTGGTCC-CTCACCCCGGG-3'; SEQ ID NO:7) and downstream primer (5'-GCTCTAGAGCTTATGTAGTGCCTGGG-TCCTGAGAGTCTT-3'; SEQ ID NO:8). The 5' region of the upstream primer contains the last 27 nucleotides of the sequence coding for α-factor signal peptide from the pPICZα A vector (Invitrogen, San Diego, Calif., USA), and incorporates an XhoI restriction site at the 5' end of the amplified product. The downstream primer incorporates a transcription stop codon and an XbaI restriction site at the 3' end of the amplified product.

The amplified product was isolated using the Wizard® PCR Preps DNA Purification System kit (Promega, Madison, Wis., USA), digested with XhoI and XbaI restriction endonucleases (Gibco BRL, Grand Island, N.Y., USA) and ligated into the XhoI and XbaI-sites of the pPICZα A vector to produce pPICZα/soluble TNF-RI. Ligations were transformed into E. coli strain Top 10F' (Invitrogen) and transformants selected according to recommended procedure (Invitrogen). Recombinant clones were analyzed for the presence of insert by restriction digestion, and sequenced to confirm the integrity of the constructs.

SacI-linearized pPICZα plasmid DNA containing nucleic acid sequences encoding the soluble bovine TNF-RI (5 mg/transformation) was used to chemically transform P. pastoris strains GS115 and KM71 (Invitrogen) according to the Easy Comp™ Pichia transformation kit protocol (Invitrogen). Integration of vector DNA into the Pichia genome was confirmed by PCR using 5'AOX1 and 3'AOX1 primers as described in the EasySelect™ Pichia Expression Kit protocols (Invitrogen). The methanol utilization (Mut) phenotypes of Zeocin-resistant (Invitrogen) transformants from the GS115 transformation reaction were also analyzed according to the EasySelect™ Pichia Expression Kit protocols.

Expression of soluble bovine TNF-RI was performed in baffled shake flasks (Sigma, St. Louis, Mo., USA) according to recommended procedure (EasySelect™ Pichia Expression Kit protocols). Buffered glycerol-complex medium (BMGY) was used for the generation of biomass and buffered methanol-complex medium (BMMY) for induction of protein expression. To maintain induction, 100% methanol was added to a final concentration of 1% every 24 h. To purify the soluble bovine TNF-RI, Pichia culture supernatants were concentrated using Centricon Plus-80 concentrators (Millipore, Bedford, Mass., USA) and dialyzed overnight at 4° C. against column equilibration buffer (10 mM Tris-HCl, 25 mM NaCl, 10 mM β-mercaptoethanol, pH 8.0). They were then loaded onto 20 ml columns of diethylaminoethyl (DEAE)-sephacel (Sigma) previously equilibrated in the same buffer. Bound proteins were eluted using a NaCl gradient (0–500 mM) in 10 mM Tris-HCl, pH 8.0. Protein in each fraction was confirmed by monitoring absorbance at $A_{280}$. Fractions containing soluble bovine TNF-RI were pooled, concentrated using a Centriprep-10 concentrator (Millipore) and stored at −70° C. Five hundred μl of culture supernatants were concentrated to 15 μl, and the entire volume loaded onto an SDS-PAGE for analysis of the *Pichia*-expressed soluble bovine TNF-RI polypeptide.

EXAMPLE 4

TNF Inhibition Assays

TNF inhibition assays were performed as described in the CellTiter 96™ Non-Radioactive Cell Proliferation Assay (Promega, Madison, Wis.) with slight modifications. Briefly, two-fold serial dilutions of soluble bovine TNF-RI or anti-bovine TNF-α monoclonal antibody (MAb) BC9 (courtesy of Dr. Jan Naessens, International Livestock Research Institute, Nairobi, Kenya) were incubated for 1 h at room temperature with equal volumes of bovine whey samples (Shuster et al., 1993, *Am. J Vet. Res.* 54:80–85) from milk obtained from quarters that had been infused with lipopolysaccharide (LPS) from *Escherichia coli* serotype 055:B5 (Sigma, St. Louis, Mo., USA). The samples were then assayed in triplicate for cytotoxicity on WEHI 164 mouse fibrosarcoma cells (clone 13), seeded at a concentration of $3 \times 10^4$ cells/well in RPMI-1640 medium (Sigma) supplemented with 10% heat-inactivated fetal bovine serum (Hyclone Laboratories, Logan, Utah) and 50 μg gentamicin/ml (Sigma). A recombinant murine TNF-α was used as a standard to calculate TNF-α cytotoxicity in the samples. Absorbances were read at a wavelength of 590 nm and corrected for background absorbances using a reference wavelength of 650 nm.

EXAMPLE 5

Therapeutic Efficacy of Soluble Bovine TNF-RI

A DNA fragment (SEQ ID NO:3) encoding 181 aa of the predicted extracellular domain of bovine TNF-RI (SEQ ID NO:4) was amplified by PCR and cloned into the pPICZαA expression vector downstream of the inducible alcohol oxidase1 (AOX1) gene promoter and in frame with the sequence coding for the α factor signal peptide. The resulting pPICZα/soluble TNF-RI construct was linearized at a unique SacI site within the 5'AOX1 region and transformed into GS115 and KM71 cells leading to integration of the vector DNA into the corresponding region of the *Pichia* genome. Integration into the *Pichia* genome was confirmed by PCR, and the Mut phenotype of GS115 integrants determined by growth on minimal methanol histidine plates. Several $Mut^+$ GS115 integrants, as well as $Mut^s$ KM71 integrants, were tested for their ability to express soluble bovine TNF-RI in small-scale expression cultures, and clones that secreted a polypeptide of the expected size (~21 kDa) upon induction with methanol, as determined by sodium dodecyl sulfate-polyacrylamide gel electrophoresis with Coomassie Blue staining, were selected and used in large-scale protein expression studies. Expressed proteins were purified to greater than 95% purity by ion-exchange chromatography and verified to be of bovine origin by Western blotting using rabbit anti-bovine whole serum that had been adsorbed with horse and pig serum proteins.

Figure 3:
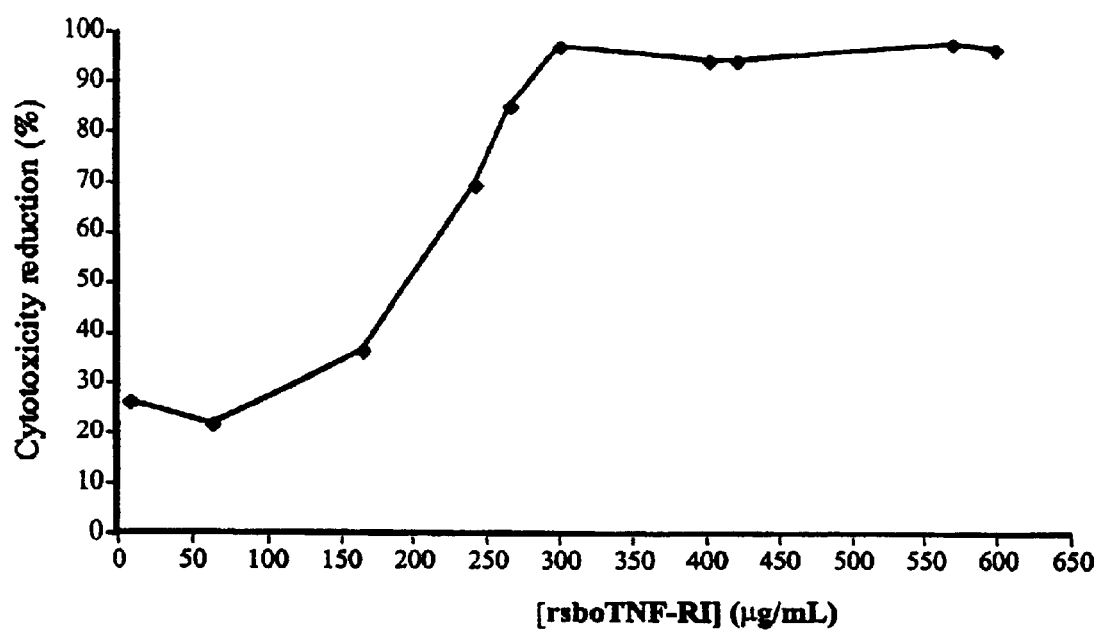
FIG. 3 is a graph demonstrating anti-bovine TNF cytotoxicity by soluble bovine TNF-RI.

Purified soluble bovine TNF-RI polypeptide was evaluated for its ability to block bovine TNF-α cytotoxicity on murine WEHI 164 cells (FIG. 3). Bovine whey samples prepared from milk obtained from quarters that had been infused with 25 μg LPS/quarter served as source of bovine TNF-α. The anti-bovine TNF-α MAb, derived from hybridoma BC9 (Sileghem et al., 1992, *Hybridoma* 11:617–627), was used as a reference for TNF-α cytotoxicity blockade. Dilutions of soluble bovine TNF-RI were incubated for 1 h at 37° C. with equal volumes of whey samples containing 6.4 U bovine TNF-α/ml. For a control, whey samples were mixed with equal volumes of medium or the anti-bovine TNF-α MAb, BC9. Fifty μl of the mixtures were added to WEHI 164 cells clone 13 and incubated for a further 20 h. 3-(4,5-dimethylthiazol-2-yl)-2,5-diphenyl tetrazolium bromide (MTT) (Sigma) was added, the samples incubated for an additional 4 h, and the reactions stopped by addition of stop/solubilization solution. Samples were then left to stand overnight at room temperature, and the conversion of MTT into a formazan product by surviving cells evaluated by measuring absorbance at 590 nm. The expressed soluble bovine TNF-RI blocked TNF-α cytotoxicity by 50% when used at a concentration of about 200 μg/ml, and 97% when used at a concentration of 300 μg/ml (FIG. 3). In contrast, MAb BC9 inhibited 85% of TNF-α cytotoxicity when used at a concentration of 900 μg/ml. Compared to the anti-bovine TNF-α monoclonal antibody BC9, soluble bovine TNF-RI exhibited greater than 2-fold more potency at blocking bovine TNF-α than did the monoclonal antibody.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A purified bovine TNF-RI polypeptide that binds bovine TNF, wherein said polypeptide is encoded by a nucleic acid selected from the group consisting of:
   (a) the nucleotide sequence of SEQ ID NO.:1;
   (b) a fragment of the nucleotide sequence of (a); and
   (c) a nucleotide sequence that is at least 85% identical to (a) or (b).

2. The polypeptide of claim 1, wherein said nucleotide sequence is at least 90% identical to (a) or (b).

3. The polypeptide of claim 1, wherein said nucleotide sequence is at least 95% identical to (a) or (b).

4. The polypeptide of claim 1, wherein said polypeptide comprises a bovine TNF-RI extracellular domain or a fragment thereof.

5. The polypeptide of claim 1, wherein said polypeptide is purified to greater than 95% purity.

6. A purified soluble bovine TNF-RI polypeptide that binds bovine TNF, wherein said polypeptide is encoded by a nucleic acid selected from the group consisting of:
   (a) the nucleotide sequence of SEQ ID NO.:3,
   (b) a fragment of the nucleotide sequence of (a); and
   (c) a nucleotide sequence that is at least 85% identical to (a) or (b).

7. The polypeptide of claim 6, wherein said polypeptide comprises a bovine TNF-RI extracellular domain or a fragment thereof.

8. The polypeptide of claim 6, wherein said nucleotide sequence is at least 90% identical to (a) or (b).

9. The polypeptide of claim 6, wherein said nucleotide sequence is at least 95% identical to (a) or (b).

10. The polypeptide of claim 6, wherein said polypeptide is purified to greater than 95% purity.

11. A purified bovine TNF-RI polypeptide, wherein said polypeptide is selected from the group consisting of:
    (a) the polypeptide of SEQ ID NO:2; and
    (b) a fragment of the polypeptide of (a) that binds bovine TNF.

12. The polypeptide of claim 11, wherein said polypeptide comprises a bovine TNF-RI extracellular domain or a fragment thereof.

13. The polypeptide of claim 11, wherein said polypeptide is purified to greater than 95% purity.

14. A purified soluble bovine TNF-RI polypeptide, wherein said polypeptide is selected from the group consisting of:
    (a) the polypeptide of SEQ ID NO:4; and
    (b) a fragment of the polypeptide of (a) that binds bovine TNF.

15. The polypeptide of claim 14, wherein said polypeptide comprises a bovine TNF-RI extracellular domain or a fragment thereof.

16. The polypeptide of claim 14, wherein said polypeptide is purified to greater than 95% purity.

* * * * *

UNITED STATES PATENT AND TRADEMARK OFFICE
CERTIFICATE OF CORRECTION

PATENT NO. : 6,939,950 B2 Page 1 of 1
APPLICATION NO. : 09/970532
DATED : September 6, 2005
INVENTOR(S) : Taylor et al.

It is certified that error appears in the above-identified patent and that said Letters Patent is hereby corrected as shown below:

Title Page, Item (56), References Cited, Other Publications, please insert
--Maroushek-Boury, Thesis, 1997--

Signed and Sealed this

Nineteenth Day of February, 2008

JON W. DUDAS
*Director of the United States Patent and Trademark Office*